United States Patent [19]

Drent

[11] Patent Number: 4,960,926
[45] Date of Patent: Oct. 2, 1990

[54] PROCESS FOR THE CARBONYLATION OF OLEFINICALLY UNSATURATED COMPOUNDS WITH A PALLADIUM CATALYST

[75] Inventor: Eit Drent, Amsterdam, Netherlands

[73] Assignee: Shell Oil Company, Houston, Tex.

[21] Appl. No.: 386,035

[22] Filed: Jul. 27, 1989

Related U.S. Application Data

[63] Continuation of Ser. No. 123,516, Nov. 20, 1987, abandoned.

[30] Foreign Application Priority Data

Dec. 24, 1986 [NL] Netherlands ................. 8603302

[51] Int. Cl.$^5$ .................................. C07C 67/38
[52] U.S. Cl. .................................. 560/233; 260/410; 558/353; 560/105; 560/114; 560/155; 560/187; 560/179; 560/204; 562/406; 562/497; 562/522; 562/890
[58] Field of Search ............... 560/105, 114, 155, 179, 560/187, 204, 233; 562/406, 497, 522, 890; 558/353; 260/410.9 C, 413 HC

[56] References Cited

U.S. PATENT DOCUMENTS

| | | | |
|---|---|---|---|
| 3,168,553 | 2/1965 | Slaugh | 560/233 |
| 3,437,676 | 4/1969 | Kutepow | 560/233 |
| 3,776,929 | 12/1973 | Mrowca | 560/233 |
| 4,124,617 | 11/1978 | Knifton | 562/522 |
| 4,536,340 | 8/1985 | Hanes | 560/233 |
| 4,739,110 | 4/1988 | Drent | 562/522 |

FOREIGN PATENT DOCUMENTS 0063818 11/1982 European Pat. Off. .
0106379 4/1984 European Pat. Off. .

*Primary Examiner*—Michael L. Shippen

[57] ABSTRACT

Process for the carbonylation of olefinically unsaturated compounds with carbon monoxide in the presence of a hydroxyl-group-containing compound, a palladium catalyst, an organic phosphine, an acid with a pKa value <2, with the exception of halogen acids and carboxylic acids as promoter, and a catlayst stabilizer selected from the group consisting of compounds of the general formula;

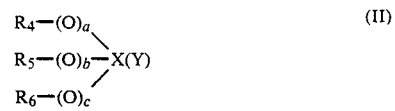

(II)

wherein X represents an element of group Va with a valency greater than 3, selected from P. As or Sb, where Y represents an element of group VIa, selected from O, S or Se, and where either a, b and c are 0 or 1, where $R_4$, $R_5$ and $R_6$ are the same or different and represent hydrocarbon groups, or a and b=0 and c=0 or 1 and $R_4$ and $R_5$ together with X form a heterocyclic group, or a, b and c=0 and $R_4$, $R_5$ $R_6$ together with X form a heterocyclic group, compounds of the general formula:

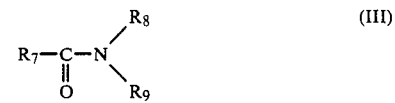

(III)

wherein $R_7$ is a hydrocarbon group and where $R_8$ and $R_9$ are each the same or different and have the aforesaid meaning of $R_7$ or together with N form a heterocyclic ring, or where $R_7$ and $R_8$ or $R_9$ together with the residue

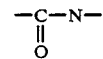

form a heterocyclic ring such as a pyrrolidon or caprolactam ring and mixtures thereof.

27 Claims, No Drawings

PROCESS FOR THE CARBONYLATION OF OLEFINICALLY UNSATURATED COMPOUNDS WITH A PALLADIUM CATALYST

This is a continuation of application Ser. No. 123,516 filed Nov. 20, 1987, now abandoned.

FIELD OF THE INVENTION

The invention relates to a process for the carbonylation of olefinically unsaturated compounds with a palladium catalyst. In particular, the invention relates to a process for the conversion of olefinically unsaturated compounds with carbon monoxide in the presence of a hydroxyl-group-containing compound such as water, alcohols or carboxylic acid under the formation of carboxylic acids, esters or carboxylic acid anhydrides respectively.

BACKGROUND OF THE INVENTION

Known carbonylation processes, such as that disclosed in U.S. Pat. No. 3,437,676, have the drawback that relatively high pressures are necessary, while in addition the conversion rates are relatively low, which leads to long reaction times. This makes them unattractive for application on a technical scale.

European patent application No. 0106379 discloses a process for the carbonylation of propene in the presence of water or an alkanol and a catalyst, composed of palladium or a compound thereof, a triaryl phosphine and an acid as promotor. Although the reaction rate appears to be considerably increased relative to the aforementioned processes, a part of the promoter acid is lost during the course of the reaction, which results in deactivation of the catalyst system employed.

It has now been found that the reaction rate of the conversion can be maintained for a considerable time at the desired level by employing a catalyst stabilizer in catalytic quantities.

SUMMARY OF THE INVENTION

The invention relates to an improved process for the carbonylation of olefinically unsaturated compounds which comprises reacting said olefinically unsaturated compounds with carbon monoxide in the presence of a hydroxyl-group-containing compound such as water, an alcohol or a carboxylic acid, a palladium catalyst, an organic phosphine according to the formula

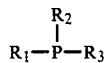

(I)

where $R_1$, $R_2$ and $R_3$ each represent an optionally substituted aryl group, an acid with a pKa value <2, with the exception of halogen acids and carboxylic acids, as promoter, and a catalyst stabilizer selected from the group consisting of compounds of the general formula:

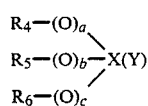

(II)

wherein X represents an element of Group VA with a valency greater than 3, selected from P, As or Sb, wherein Y represents an element of Group VIA, selected from O, S or Se, and wherein a, b and c are 0 or 1 and $R_4$, $R_5$ and $R_6$ are the same or different and represent optionally substituted hydrocarbon groups, a and b=0 and c=0 or 1 and $R_4$ and $R_5$ together with X form a heterocyclic group, or a, b and c=0 and $R_4$, $R_5$ and $R_6$ together with X form an optionally substituted heterocyclic aromatic group, compounds of the general formula:

(III)

wherein $R_7$ represents an optionally substituted hydrocarbon group and wherein $R_8$ and $R_9$ are each the same or different and have the aforesaid meaning of $R_7$ or together with N form an optionally substituted heterocyclic ring or wherein $R_7$ and $R_8$ or $R_9$ together with the residue

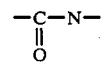

form a heterocyclic ring such as a pyrrolidon or caprolactam ring and mixtures thereof.

DESCRIPTION OF THE PREFERRED EMBODIMENTS

The aforesaid hydrocarbon groups in the definitions of $R_4$ to $R_9$ can he alkyl, cycoalkyl, aryl, aralkyl or alkaryl groups containing up to 30 carbon atoms. As used herein, the terms "hydrocarbon groups" and "heterocyclic groups" refer to unsubstituted groups as well groups having any number of substituents which do not interfere in the reaction. If $R_4$ and $R_5$ or $R_5$ and $R_6$ or $R_8$ and $R_9$ or $R_7$ and $R_8$ or $R_9$ form a heterocyclic group with X in formula (11) or N or —C—N— in formula (II) respectively, the hydrocarbon residue of the heterocyclic group can contain up to 21 carbon atoms. The preferred compounds according to formula (1) are those where a, b and c=0, where X=P, where Y=0 or S and where $R_4$, $R_5$ and $R_6$ represent alkyl groups which comprise 1-4 carbon atoms, or cycloalkyl, aryl or aralkyl groups which comprise 5-12 carbon atoms and are preferably alky, phenyl, cycohexyl or benzyl groups. In more preferred groups according to formula (II), Y represents oxygen, while $R_4$, $R_5$ and $R_6$ represent alkyl groups or Y represents sulphur, while $R_4$, $R_5$ represent phenyl groups which can be unsubstituted or substituted. The substituents, if any, on the hydrocarbon groups and/or the heterocyclic groups should in fact be inert in the reaction medium. Suitable substituents are, for example, chlorine, alkoxy groups, carboxylic acid (ester) groups or sulfonic or sulfoxide groups.

Examples of suitable stabilizers according to formula (II) are oxides, sulfides or selenides or tertiary phosphines or the corresponding arsenic or antimony derivatives, such as trimethyl phosphine oxide, triethyl phosphine oxide, tri-n-propyl phosphine oxide, tri-n-butyl phosphine oxide, triphenyl phosphine oxide, tri-p-tolyl phosphine oxide, tri-p-tolyl phosphine sulphide, tricyclohexyl phosphine oxide, diphenyl ethyl phosphine oxide, tri(1-naphthyl) phosphine oxide, tri(1-naphthyl) phosphine sulfide, 1-phenyl phosphalane sulfide, 1-phenyl phosphorinane sulfide, trimethyl phosphine sulfide, tri-4-chlorophenyl phosphine sulfide, triphenyl phosphine sulfide, tricyclohexyl phosphine sulfide, tri-n-butyl phosphine sulfide, triphenyl phosphine selenide, tri(1-naphthyl) phosphine selenide and triphenyl arsine sulfide. Of these, tri-p-tolyl phosphine sulfide, triphenyl phosphine sulfide, tricyclohexyl phosphine sulfide, tri-n-butyl phosphine oxide, trimethyl phosphine oxide, tri-n-propyl phosphine oxide and triethyl phosphine oxide are preferred.

Other examples of suitable stabilizers according to formula (II) are alkyl and aryl esters of phosphoric acid, phosphonic acid and phosphinic acids and their arsenic or antimony analogues such as trimethyl phosphate, triethyl phosphate, tri-n-butyl phosphate, triphenyl phosphate, dimethyl methyl phosphonate, 1,5-dimethyl bicyclo(3,2,1,) octyl octyl phosphonate, diethyl methyl phosphonate and methyl diphenyl phosphonate. Preferably, phosphonates are employed.

It will he appreciated that according to another embodiment of the process according to the invention, stabilizers can also be used that can comprise two or more groups, represented by formula (II).

Examples of such stabilizers are:
tetraphenyl ethylene diphosphine disulfide,
tetraphenyl methylene diphosphine disulfide,
tetramethyl ethylene diphosphine dioxide,
tetraphenyl propylene diphosphine disulfide,
tetraphenyl butylene diphosphine disulfide,
tetraethyl ethylene diphosphine dioxide,
tetrapropyl ethylene diphosphine dioxide,
tetraethyl propylene diphosphine dioxide,
tetraethyl butylene diphosphine dioxide,
tetramethyl butylene diphosphine dioxide and
tetramethyl propylene diphosphine dioxide.

The preferred stabilizers according to general formula (III) are those wherein $R_7$, $R_8$ and $R_9$ represent an alkyl of 1-4 carbon atoms, a cycloalkyl, cycloalkaryl, aryl or aralkyl group comprising 5-12 carbon atoms, and preferably alkyl, phenyl, benzyl or cyclohexyl groups, or where $R_7$, $R_8$ or $R_9$ together with the residue

form a heterocyclic ring.

Examples of suitable stabilizers according to formula (II) are
N,N'-dimethyl acetamide, N,N'-diethyl acetamide, N,N'-diethyl propionamide, N,N'-diethyl butamide, N,N'-dipropyl propionamide, N,N'-di(isopropyl)propionamide, N,N'-di(isopropyl) acetamide, N,N'-diphenyl acetamide, N-methyl pyrrolidone and N-methyl caprolactam.

It will be appreciated that according to another embodiment of the process according to the invention, stabilizers can also be used that can comprise two or more groups, represented by formula (11). Examples of such stabilizers are
N,N,N'N'-tetramethyl malonamide,
N,N,N'N'=tetraethyl malonamide,
N,N,N'N'-tetramethyl succinamide and
N,N,N'N'-tetraethyl succinamide, It will be aPPreciated that each of the aforesaid stabilizers can be employed as such or in combination with one or more others.

The quantity of catalyst stabilizer according to formulas (II) and (III) that can be used in the process according to the invention can vary from 0.01 mol to 200 mol per gram-atom palladium. The acids that can be used as promoters for the process according to the invention preferably comprise a non-coordinating anion, by which is meant that little or no covalent interaction takes place between the palladium and the anion. Typical examples of such anions are $PF_6^-$, $SbF_6^-$, $BF_4^-$ and $ClO_4^-$. Preferably employed acids are, for example, sulfonic acids and acids that can be formed, possibly in situ, by the interaction of a Lewis acid such as $BF_3$, $AsF_5$, $SbF_5$, $PF_5$, $TaF_5$ or $NbF_5$ with a Bronsted acid such as a hydrohalogenic acid, in particular hydrofluoric acid, fluorosulfonic acid, phosphoric acid or sulfuric acid. Specific examples of the latter type of acids are $H_2SiF_6$, $HBF_4$, $HPF_6$ and $HSbF_6$. Typical sulfonic acids that can be used as fluorosulfonic acid, chlorosulfonic acid and the sulfonic acids specified below. A preferred group of acids has the general formula

(IV)

where Q represents sulfur or chlorine and where, if Q is chlorine, $R_{10}$ represents oxygen and if Q is sulphur, R represents an OH-group or a substituted or unsubstituted hydrocarbon group.

If the aforesaid acids are employed in the process according to the invention, the anions of the acids can be considered as non-coordinating.

The carbonylation of the olefinically unsaturated compounds should preferably be carried out in the presence of both an acid specified above and at least 5 mol of the said phosphine. In the acids according to formula (IV), the hydrocarbon group in the definition of $R_{10}$ is preferably an alkyl, aryl or aralkyl group with 1-30 and preferably 1-14 carbon atoms. The hydrocarbon can be substituted with, for example, halogen atoms, in particular fluorine atoms. Examples of suitable acids according to formula (IV) are perchloric acid, sulfuric acid, 2-hydroxypropane-2-sulfonic acid, p-toluene sulfonic acid and trifluoromethane sulfonic acid, of which the last two acids are preferred. The acid according to formula (V) can also be an ion exchanger comprising sulfonic acid groups such as Amberlite 252 $H^R$. In this case, the hydrocarbon group $R_{10}$ consists of a polymeric hydrocarbon group substituted with sulfonic acid groups, for example a polystyrene polymer with sulfonic acid groups. The quantity of the acid present in the reaction mixture is preferably 0.10-150, and in particular 0.1-100, and more preferably 1-50 equivalents per gram-atom palladium. The acid can optionally be formed in situ for example by hydrolysis of an ester such as an alkyl ester of a sulfonic acid or by the reaction of a ketone with $SO_2$ and water.

It will be appreciated that by employing the process according to the invention high reaction rates can be achieved which, during the course of the carbonylation reaction, can be maintained practically at the initial level, thus leading to shorter reaction times and making this process ideally suited to continuous processes. Moreover, this stabilization leads to reduced catalyst consumption and thus to lower costs for the preparation of, for example, methyl propionate from ethene, which makes this process a considerable improvement for batchwise, semi-continuous and continuous processes.

The olefinically unsaturated compounds to be converted can be unsubstituted or substituted alkenes or cycloalkenes, which preferably comprise 2-30 and in particular 2-20 carbon atoms. Preferably, these starting compounds comprise 1-3 double bonds. The alkenes or cycloalkenes can, for example, be substituted with one or more halogen atoms or cyano, ester, alkoxyl, hydroxyl, carboxyl or aryl groups. If the substituents are not inert under the reaction conditions, the carbonylation reaction may be accompanied by other reactions. For example, the carbonylation of alkyl alcohol may be accompanied by esterification of the hydroxyl group. Examples of suitable olefinic compounds are ethene, propene, butene-1, butene-2, isobutene, the isomeric pentenes, hexenes, octenes and dodecenes, 1,5-cyclooctadiene, cyclododecene, 1,5,9-cyclododecatriene, ally alcohol, methyl acrylate, ethyl acrylate, methyl methacrylate, acrylonitrile, acrylamide, N,N-dimethyl acrylamide, vinyl chloride, allyl chloride, acroleine, oleic acid, linoleic acid, methyl allyl ether and styrene.

The alcohols or carboxylic acids used in the process according to the invention can be aliphatic, cycloaliphatic or aromatic and can be substituted with one or more substituents such as mentioned hereinbefore in connection with the olefinically unsaturated compounds which can be used as starting material. The alcohol can therefore also be a phenol. The alcohols or carboxylic acids preferably comprise no more than 20 carbon atoms. Examples of suitable alcohols or carboxylic acids are methanol, ethanol, propanol, isobutanol, tert. butanol, stearyl alcohol, benzyl alcohol, cyclohexanol, allyl alcohol, chlorocapryl alcohol, ethylene glycol, 1,2-propane diol, 1,4-butane diol, glycerol, polyethylene glycol, 1,6-hexane diol, phenol, cresol, acetic acid, propionic acid, butyric acid, capronic acid, trimethyl acetic acid, benzoic acid, caprylic acid, adipic acid and hydroxycapronic acid.

Particular preference is given to alkanols nd carboxylic acids of 1-10 carbon atoms. If the alcohol or the carboxylic acid comprises more than one hydroxyl group or carboxylic acid group, various products can be formed, depending on the molar ratios of the reagents. For example, a monoester or a diester can be formed for gycerol, depending on the used quantity of olefinically unsaturated compound.

The products formed by the process according to the invention can, if desired, be converted further. For example, if the carbonylation of an olefin is carried out in the presence of water, a carboxylic acid can be formed that can, by the reaction of an additional quantity of olefin, form a carboxylic acid anhydride. If the carbonylation is carried out in the presence of an alcohol, an ester is formed which, if water is also present, can hydrolyze to form an acid and an alcohol, which can then again each react with an olefin. If the carbonylation is carried out in the presence of a carboxylic acid, an acid anhydride is formed which, if water is also present, can hydrolyze to form or more carboxylic acids which in turn can react further with a quantity of olefin. The reaction of an alkane carboxylic acid comprising n+1 carbon atoms with an olefin comprising n carbon atoms forms the symmetric anhydride of the alkane carboxylic acid with n+1 carbon atoms. This anhydride can be optionally hydrolyzed, whereby half of the carboxylic acid formed as a product can be collected and the other half can be returned to the carbonylation reactor. The process thus leads to the conversion of an olefin with n carbon atoms to a carboxylic acid of n+1 carbon atoms.

Both homogeneous and heterogeneous palladium catalysts can be employed in the process according to the invention. Homogeneous catalysts are, however, preferred. Suitable homogeneous catalyst are palladium salts of nitric acid, sulfuric acid or alkane carboxylic acids with not more than 12 carbon atoms per molecule. Salts of halogen acids can in principle also be employed, but these have the drawback that the halide ion can have a corrosive effect. Preferably, palladium acetate is used as catalyst. Palladium complexes, such as palladium acetyl acetonate, tetrakis triphenyl phosphine palladium, bus-tri-O-toly phosphine palladium acetate or bis-triphenyl phosphine palladium sulfate, can also be used. Palladium on active carbon or bonded to an ion-exchanger, for example an ion exchanger comprising sulfonic acid groups, are examples of a suitable heterogeneous catalyst.

The quantity of the palladium compound is not critical. Preferably, quantities are employed in the range of $10^{-5}$ to $10^{-1}$ gram-atom palladium per mol olefinically unsaturated compound.

The substituted or unsubstituted aryl groups $R_1$, $R_2$ and $R_3$ in formula (I) preferably comprise not more than 18 carbon atoms, and in particular 6-14 carbon atoms. Examples of suitable $R_1$, $R_2$ and $R_3$ groups are the naphthyl group and more preferably the phenyl group. Suitable substituents are halogen atoms and akyl, aryl, alkoxy, carboxy, carbalkoxy, acyl, trihalogenomethyl, cyano, dialkyl amino, sulphonyl alkyl and alkaroyloxy groups.

Examples of suitable phosphines are triphenyl phosphine, tri-p-methoxyphenyl phosphine, o-diphenyl phosphino benzoic acid and in particular triphenyl phosphine. The phosphine is used in a quantity of at least 5 mol and preferably 10-150 mol per gram-atom palladium. If the palladium catalyst already comprises phosphine, this should be taken into account when calculating the phosphine to be employed.

In the process according to the invention, the carbon monoxide can be used in a pure form or diluted with an inert gas, such as hydrogen, nitrogen, rare gases or carbon dioxide. In general, the presence of more than 10% hydrogen is undesirable, since this gas can cause hydrogenation of the olefinic compound under the reaction conditions. The carbonylation according to the invention is preferably performed at a temperature in the range of 50° C. to 200° C. and in particular between 75° C. and 150° C. he total pressure preferably lies between 1 and 100 bar, and more in particular between 20 and 75 bar overpressure.

The molar ratio of the olefinically unsaturated compound to water, alcohol or carboxylic acid is not critical. The molar ratio of the hydroxyl-group-containing compound to olefinic double bonds can lie, for example, between 0.1:1 and 10:1. If a mono-olefin and/or water, a monohydric alcohol or a monobasic acid is applied, the use of an excess of the aforementioned hydroxyl-compound is preferred. If, however, a polyhydric alcohol or a polybasic acid is employed to prepare a polyester or a polyanhydride, it will in general be necessary to use an excess of the olefinic compound.

The process according to the invention can be performed batchwise, continuously or semi-continuously.

In general, no separate solution is needed, since there will usually be an excess of one of the reactants, for example the alcohol, which can also function as solvent.

If desired, however, a solvent can be employed, for example benzene, xylenes, toluene, anisole, diisopropyl sulfone, sulfolane, acetone, chloroform, methyl isobutyl ketone, diglym (dimethyl ether from diethylene glycol), diphenyl ether or diisopropyl ether. The primary reaction product of the carbonylation reaction can also be used as solvent.

It will be appreciated that another facet of the present invention is formed by the aforesaid catalyst systems, which are employed for the selective conversion of the olefinically unsaturated compounds, as such or in the form of a solution in one or more of the suitable aforesaid solvents.

Although the application of a number of the compounds according to formula (11) in catalyst systems is known from, for example, European patent application No. 0108437, it will be appreciated that the catalyst systems employed herein comprise completely different components (bromide or iodide sources), while the reaction system comprises entirely different reactants and the conversion is of a quite different type.

The invention will now be explained with reference to the following examples, without however restricting the scope of the invention of these embodiments.

EXAMPLE 1

A 250 ml magnetically stirred Hastelloy $C^R$ autoclave was filled with 10 ml methanol, 50 ml methyl proprionate, 0.1 mmol palladium acetate, 3 mmol triphenyl phosphine, 2 mmol p-toluene sulfonic acid and 10 mmol tributyl phosphine oxide. The autoclave was purged with carbon monoxide and filled with ethene to a pressure of 20 bar and carbon monoxide to a pressure of 30 bar, closed and heated to a temperature of 110° C. After a reaction time of 5 hours, the autoclave contents were analyzed by gas-liquid chromatography. The starting acid (p-toluene sulfonic acid) still present was determined with the aid of potentiometric titration with a base (NaOH/methanol mixtures). The methanol to methyl propionate conversion was 48%. The selectivity of the conversion of ethene to methyl propionate was found to be almost 100%, while the average conversion rate was 240 ml per gram-atom Pd per hour.

EXAMPLE 2

In a virtually analogous manner to that described in Example 1, an experiment was performed in which 5 mmol instead of 10 mmol tributyl phosphine oxide was added. The reaction time was 2.5 hours. The methanol to methyl propionate conversion was 48%. The initially added acid was found by means of the method mentioned in Example 1 to be still present in its entirety in the reaction mixture. The selectivity of the ethene to methyl propionate conversion was found to be almost 100%, while the average conversion rate was 480 mol per gram-atom Pd per hour.

EXAMPLE 3

In a virtually analogous manner to that described in Example 1, an experiment was performed in which 2 mmol instead of 10 mmol tributyl phosphine oxide was added. The reaction time was 2.5 hours. The initially added acid was found by the aforesaid method to be still present almost in its entirety (>95%) in the reaction mixture. The methanol to methyl propionate conversion was 90%. The selectivity of the ethene to methyl propionate conversion was found to be almost 100%, while the average conversion rate was 900 mol per gram-atom Pd per hour.

EXAMPLE 4

In a virtually analogous manner to that described in Example 1, an experiment was performed in which 2 mmol triphenyl phosphine sulfide was employed. The reaction time was 1.5 hours. The methanol to methyl propionate conversion was 93%. At the end of the reaction, the initially added acid was found by the aforesaid method to be still present in almost its entirety in the reaction mixture. The selectivity of the ethene to methyl propionate conversion was found to be almost 100%, while the average conversion rate was 1550 mol per gram-atom Pd per hours.

COMPARATIVE EXPERIMENT A

A comparative experiment was carried out in the same way as Example 4, but with a reaction time o& 0.5 hours. The initially added acid was found by the aforesaid method to be still present in almost its entirety in the reaction mixture. The methanol to methyl propionate conversion was 40%. The selectivity of the ethene to methyl propionate conversion was found to be almost 100%, while an average conversion rate of 2000 mol per gram-atom Pd per hour was found.

EXAMPLE 5

In a virtually analogous manner to that described in Example 1, an experiment was performed in which 0.5 ml triphenyl phosphine sulfide was employed. The reaction time was 1.5 hours. The methanol to methyl propionate conversion was 98%. The initially added acid was found by the aforesaid method to be still present in almost (>95%) its entirety in the reaction mixture. The selectivity of the ethene to methyl propionate conversion was found to be almost 100%, while the average conversion rate was 1640 mol per gram-atom Pd per hour.

EXAMPLE 6

In a virtually analogous manner to that described in Example 1, an experiment was performed in which 5 mmol triphenyl phosphine sulfide was employed. The reaction time was 2.5 hours. The methanol to methyl propionate conversion was 92%. The initially added acid was found by the aforesaid method to be still present in its entirety in the reaction mixture. The selectivity of the ethene to methyl propionate conversion was found to be almost 100% while the average conversion rate was 920 mol per gram-atom Pd per hour.

EXAMPLE 7

In a virtually analogous manner to that described in Example 1, an experiment was performed in which 10 mmol N-methyl pyrrolidone was employed. The reaction time was 2.5 hours. The methanol to methyl propionate conversion was 93%. The initially added acid was found by the aforesaid method to be still present in its entirety in the reaction mixture. The selectivity of the ethene to methyl propionate conversion was found to be almost 100% while the average conversion rate was 930 mol per gram-atom Pd per hour.

EXAMPLE 8

In a virtually analogous manner to that described in Example 1, an experiment was performed in which 5 mmol diphenyl acetamide was employed. The reaction time was 2.5 hours. The methanol to methyl propionate conversion was 99%. The initially added acid was found by the aforesaid method to be still present almost (>85%) in its entirety in the reaction mixture. The selectivity of the ethene to methyl propionate conversion was found to be almost 100% while the average conversion rate was 1000 mol per gram-atom Pd per hour.

COMPARATIVE EXPERIMENT B

A comparative experiment was performed in the same way as Example 8 under identical conditions and with the same reaction time of 2.5 hours, but without a stabilizer. The methanol to methyl propionate conversion was now 95%. At the end of the reaction only 35% of the initially added acid was found by the aforesaid method. The selectivity of the ethene to methyl propionate conversion was found to be almost 100%, while the average conversion rate was 900 mol per gram-atom Pd per hour.

COMPARATIVE EXPERIMENT C

A comparative experiment was performed in the same way as Example 8 under identical conditions, but without a stabilizer and with a reaction time of 0.5 hours. The methanol to methyl propionate conversion was now 50%, while only 50% of the initially added acid was found by the aforesaid method in the reaction mixture. The selectivity of the ethene to methyl propionate conversion was almost 100%, while the average conversion rate was 2500 mol per gram-atom Pd per hour.

From the results of the described experiments in Examples 4 and 8, and comparative Experiments A, B and C, it is clear that the average conversion rate, drops relatively much more sharply in the absence of a stabilizer according to the present invention than in the presence of such a stabilizer.

I claim:

1. A process for the carbonylation of olefinically unsaturated compounds which comprises reacting at a temperature in the range of 50° C. to 200° C. and a pressure in the range of 1 bar to 100 bar said olefinically unsaturated compounds with carbon monoxide and a hydroxyl-group-containing selected from the group consisting of water, alcohols, carboxylic acids and mixtures thereof to form the corresponding carboxylic acids, esters or carboxylic acid anhydrides in the presence of a palladium catalyst, an organic phosphine according to the formula:

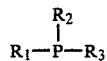
(I)

where $R_1$, $R_2$ and $R_3$ each represent an optionally substituted aryl group, an acid with a pKa value <2, with the exception of halogen acids and carboxylic acids, as promoter, and a catalyst stabilizer selected from the group consisting of compounds of the general formula:

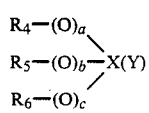
(II)

wherein X represents an element of Group VA with a valency greater than 3, selected from the group consisting of P, As and Sb, wherein Y represents an element of Group VIA selected from the group consisting of O, S and Se, and wherein, a, b and c are 0 or 1 and $R_4$, $R_5$ and $R_6$ are the same or different and represent substituted or unsubstituted hydrocarbon groups, a and b=0 and c=0 or 1 and $R_4$ and $R_5$ together with X form a heterocyclic group, or, a, b and c=0 and $R_4$, $R_5$ and $R_6$ together with X form a heterocyclic group, compounds of the general formula:

(III)

wherein $R_7$ is a hydrocarbon group and $R_8$ and $R_9$ are each the same or different and have the aforesaid meaning of $R_7$, $R_8$ and $R_9$ together with N form a heterocyclic ring, or, $R_7$ and $R_8$ or $R_9$ together with the residue

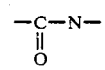

form a heterocyclic ring and mixtures of compounds represented by formula (II) and (III).

2. The process of claim 1 wherein said hydrocarbon groups as used to define $R_5$, $R_5$, $R_6$, $R_7$, $R_8$ and $R_9$ are selected from the group consisting of alkyl, cycloalkyl, aryl, aralkyl and alkaryl groups having up to about 30 carbon atoms, and mixtures thereof.

3. The process of claim 1 wherein said heterocyclic group has up to about 21 carbon atoms.

4. The process of claim 1 wherein said catalyst stabilizer is a compound of formula (II).

5. The process of claim 4 wherein a, b and c=0, wherein X is phosphorus, wherein Y is oxygen or sulfur and wherein $R_4$, $R_5$ and $R_6$ are selected from the group consisting of alkyl groups having 1 to about 4 carbon atoms, and cycloalkyl, aryl and aralkyl groups having about 5 to about 12 carbon atoms.

6. The process of claim 5 wherein Y represents oxygen and $R_4$, $R_5$ and $R_6$ represent alky groups.

7. The process of claim 5 wherein Y represents sulfur and $R_4$, $R_5$ and $R_6$ represent phenyl groups.

8. The process of claim 1 wherein $R_4$, $R_5$ and $R_6$ are hydrocarbon group substituted with one or more substituents selected from the group consisting of chlorine, alkoxy groups, carboxylic acid (ester) groups, sulfonic groups, sulfoxide groups and mixtures thereof.

9. The process of claim 4 wherein said catalyst stabilizer is selected from the group consisting of trimethyl phosphine oxide, triethyl phosphine oxide, tri-n-propyl phosphine oxide, tri-n-butyl phosphine oxide, triphenyl phosphine oxide, tri-p-tolyl phosphine oxide, tri-p-tolyl phosphine sulfide, tricyclohexyl phosphine oxide, tricyclohexyl Phosphine sulfide, diphenyl ethyl phosphine oxide, tri(1-naphthyl) lphosphine oxide, tri(1-naphthyl) phosphine sulfide, 1-phenyl phosphalane sulfide, 1-phenyl phosphorinane sulfide, trimethyl phosphine sulfide, tri-4-chlorophenyl phosphine sulfide, triphenyl phosphine sulfide, tri-n-butyl phosphine sulfide, triphenyl arsine sulfide, triphenyl phosphine selenide, tri(1-naphthyl) phosphine selenide and mixtures thereof.

10. The process of claim 9 wherein said catalyst stabilizer is selected from the group consisting of triphenyl phosphine sulfide, tri-p-tolyl phosphine sulfide, tricyclohexyl phosphine sulfide, tri-n-butyl phosphine oxide, trimethyl phosphine oxide, tri-n-propyl phosphine oxide, triethyl phosphine oxide and mixtures thereof.

11. The process of claim 4 wherein said catalyst stabilizer is selected from the group consisting of
tetraphenyl ethylene diphosphine disulfide,
tetraphenyl methylene diphosphine disulfide,
tetramethyl ethylene diphosphine dioxide,
tetraphenyl propylene diphosphine disulfide,
tetraphenyl butylene diphosphine disulfide,
tetraethyl ethylene diphosphine dioxide,
tetrapropyl ethylene diphosphine dioxide,
tetraethyl propylene diphosphine dioxide,
tetraethyl butylene diphosphine dioxide,
tetramethyl butylene diphosphine dioxide,
tetramethyl propylene diphosphine dioxide and mixtures thereof.

12. The process of claim 1 wherein said catalyst stabilizer is a compound of formula (III).

13. The process of claim 12 wherein $R_7$, $R_8$ and $R_9$ are selected from the group consisting of alkyl groups having 1 to about 4 carbon atoms, and cycloalkyl, cycloalkaryl, aryl and aralkyl groups having about 5 to about 12 carbon atoms.

14. The process of claim 12 wherein $R_7$, $R_8$ or $R_9$ together with the residue

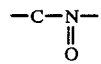

form a heterocyclic ring.

15. The process of claim 12 wherein said catalyst stabilizer is selected from the group consisting of
N,N'-dimethyl acetamide, N,N'-diethyl acetamide, N,N'-diethyl propionamide, N,N'-diethyl butamide, N,N'-dipropyl propionamide, N,N'-di(isopropyl)propionamide, N,N'-di(isopropyl) acetamide, N,N'-diphenyl acetamide, N-methyl pyrrolidone, N-methyl caprolactam and mixtures thereof.

16. The process claim 12 wherein said catalyst stabilizer is selected from the group consisting of
N,N,N'N'-tetramethyl malonamide,
N,N,N'N'-tetraethyl malonamide,
N,N,N'N'-tetramethyl succinamide,
N,N,N'N'-tetraethyl succinamide and mixtures thereof.

17. The process of claim 1 wherein an amount of catalyst stabilizer ranging from about 0.01 to about 200 mol per gram-atom palladium is used.

18. The process of claim 1 wherein said acid comprises a non-coordinating anion.

19. The process of claim 18 wherein said acids comprise ions selected from the group consisting of $PF_6^-$, $SbF_6^-$, $BF_4^-$ and $ClO_4^-$.

20. The process of claim 18 wherein said acid is selected from the group consisting of $H_2SiF_6$, $HSO_3F$, $HBF_4$, $HPF_6$ and $HSbF_6$.

21. The process of claim 19 wherein said acid has general formula

 (IV)

where Q represents sulfur or chlorine and where, if Q is chlorine, $R_{10}$ represents oxygen, and if Q is sulfur, $R_{10}$ represents an OH-group or hydrocarbon group.

22. The process of claim 1 wherein an amount of from about 10–150 mol of phosphine per gram-atom palladium is used.

23. The process of claim 1 wherein a quantity of acid ranging from about 0.01–150 equivalents per gram-atom palladium is used.

24. The process of claim 23 wherein a quantity of acid ranging from about 0.1–100 equivalents per gram-atom palladium is used.

25. The process of claim 1 wherein an amount ranging from 1 to about 50 equivalents of acid per gram-atom palladium is used.

26. The process of claim 1 wherein said palladium catalyst is palladium acetate.

27. The process of claim 1 wherein a quantity of palladium catalyst ranging from about $10^{-5}$ to about $10^{-1}$ gram-atom palladium per mol olefinically unsaturated compound is used.

* * * * *